United States Patent [19]

Pratt

[11] Patent Number: 5,323,787
[45] Date of Patent: Jun. 28, 1994

[54] CUSTOM FITTED MOUTHPIECE WITH MEDICATED PAD AND CONTAINER

[76] Inventor: Andrea P. Pratt, 3737 Timberglen St., Apt. 805, Dallas, Tex. 75287

[21] Appl. No.: 47,940

[22] Filed: Apr. 19, 1993

[51] Int. Cl.⁵ .............................................. A61C 5/14
[52] U.S. Cl. .................................. 128/862; 128/861; 128/859; 433/37
[58] Field of Search .............. 128/861, 862, 859, 848; 433/6, 37; 206/83

[56] References Cited

U.S. PATENT DOCUMENTS

| | | | |
|---|---|---|---|
| 2,375,645 | 5/1945 | Gordon | 206/83 |
| 2,643,652 | 6/1953 | Cathcart | 128/861 |
| 3,416,527 | 12/1968 | Hoef | 128/862 |
| 4,064,628 | 12/1977 | Weitzman | 128/861 |
| 4,697,700 | 10/1987 | Weissman | 206/83 |
| 4,802,853 | 2/1989 | Krasner | 206/83 |
| 4,867,680 | 9/1989 | Hare et al. | 433/37 |
| 4,920,984 | 5/1990 | Furumichi | 128/862 |
| 4,955,393 | 9/1990 | Adell | 128/862 |
| 4,966,319 | 10/1990 | Fleming | 206/83 |
| 5,184,718 | 2/1993 | Albert | 206/83 |
| 5,203,351 | 4/1993 | Adell | 128/861 |

OTHER PUBLICATIONS

WO91/12777, Oxman et al., Thermoplastic Custom Dental Tray, Sep. 5, 1991.

*Primary Examiner*—Robert A. Hafer
*Assistant Examiner*—Michael O'Neill
*Attorney, Agent, or Firm*—E. Michael Combs

[57] ABSTRACT

An apparatus for protecting and treating teeth including a mouthpiece and storage container is disclosed. The mouthpiece has an arcuate or U-shaped body and is molded from a thin layer of soft, absorbent, and pliable elastomeric material. A continuous U-shaped channel is dimensioned for receiving the upper teeth of a user and is formed in the body in a location adjacent its periphery for a length coextensive with the U-shaped periphery of the body. The body has an integral center portion which arches upwardly from the U-shaped channel to conform to the similarly upwardly arched or convex form of the roof of the mouth or palate of the mouthpiece user. The U-shaped channel may be enclosed and filled with encapsulated setting materials to form a permanent, form-fitting dental impression for the upper teeth of the user. A medicated pad may be adhesively positioned over the enclosed channel to relieve sore gums and teeth. The storage container is constructed of rigid polymeric material and has a U-shape complementary to that of the mouthpiece for receiving the mouthpiece and a treating fluid having sterilizing, mouth-refreshing, and medicating ingredients to soak the mouthpiece therein between uses.

9 Claims, 4 Drawing Sheets

CUSTOM FITTED MOUTHPIECE WITH MEDICATED PAD AND CONTAINER

BACKGROUND OF THE INVENTION

1. Field of the Invention

The field of the invention relates to oral protective and treatment devices, and more particularly to an apparatus including a mouthpiece and a storage container for use in the prevention of teeth gnashing or gritting, the formation and build-up of decay-causing film on the teeth, as well as preventing the generation of unpleasant mouth odors and tastes commonly described as "morning mouth".

2. Description of the Prior Art

Grinding or gnashing of the teeth is a surprisingly common occurrence during sleeping. Since it is done instinctively and subconsciously, it is almost impossible to control. Accordingly, no effective devices are presently known to prevent and overcome this problem. Further, build-up of decay-causing film on the teeth and the related production of undesirable morning breath odors and mouth tastes also occur during the average sleeping period of eight hours. In the past, the treatment for this condition was brushing and rinsing with a mouthwash prior to retiring for the night. While this treatment causes some reduction of film build-up and mouth odors and tastes, its effectiveness is time limited, i.e. not adequate to be effective for the entire sleeping period to virtually eliminate the undesirable film build-up and mouth odors and tastes.

Various oral protective and treatment devices have been utilized in the prior art. However, the uses for these devices are primarily related to blow protection in contact sports and in conjunction with testing devices for analyzing the composition of breath samples. For example, U.S. Pat. No. 3,457,916 to Wolicki sets forth a protective mouthpiece for use in contact sports. The mouthpiece has a U-shaped base member which is formed of a soft and flexible elastomeric material and is provided with a channel to receive the upper teeth. A self-setting elastomer filler may be placed in the channel to form a permanent dental impression therein which bonds to the base member.

U.S. Pat. No. 3,532,091 to Lerman discloses another mouthpiece for use in contact sports which is U-shaped and formed of elastomeric material and has a tubular body filled with a shock-absorbing fluid to protect the teeth. The fluid may be settable to provide a permanent record of the relationship between upper and lower occlusal surfaces of the teeth at initial contact.

U.S. Pat. No. 3,880,591 to Burroughs illustrates a mouthpiece used in conjunction with a breath testing device. The mouthpiece includes two elements, one element being a cup-shaped element having a wide open end for receiving the mouth of the user, and the other element comprising a stem inserted in the opposite end of the cup and connectable to an inlet of a testing device. Both elements are constructed of polymeric material.

U.S. Pat. No. 4,292,978 to Guth illustrates another mouthpiece for use with a breath analyzing instrument comprising a hollow, dome-shaped housing formed of polymeric material and constructed in two parts which are permanently bonded together. A plurality of oppositely angled partitions are provided within the housing to direct the breath of a user along a serpentine path to remove any foreign matter, saliva, and/or water vapor from the breath prior to its entry into the analyzing instrument.

As such, it may be appreciated that there continues to be a need for a new and improved oral protective and treatment device in the form of a mouthpiece and storage container which addresses both the problems of ease of use, portability, and effectiveness in construction, and in this respect, the present invention fulfills this need.

SUMMARY OF THE INVENTION

In view of the foregoing disadvantages inherent in the known types of oral protective and treatment devices now present in the prior art, the present invention provides an apparatus including a mouthpiece and a storage container wherein the mouthpiece is soaked in a cleansing fluid and mounted on the upper teeth of a user. The mouthpiece is used during sleep to prevent teeth gnashing or gritting, formation and build-up of decay-causing film on the teeth, as well as preventing the generation of unpleasant mouth odors and tastes commonly described as "morning mouth" to thereby create a clean, odor-free, and pleasant tasting mouth. The storage container is used to cleanse and sterilize the mouthpiece between uses. As such, the general purpose of the present invention, which will be described subsequently in greater detail, is to provide a new and improved mouthpiece and storage container which has all the advantages of the prior art oral protective and treatment devices and none of the disadvantages.

To attain this, the present invention comprises an apparatus for protecting and treating teeth which includes a mouthpiece and a storage container therefor as set forth herein. The mouthpiece has an arcuate or U-shaped body and is molded from a thin layer of soft, absorbent, and pliable elastomeric material. A continuous U-shaped channel is dimensioned for receiving the upper teeth of a user and is formed in the body in a location adjacent its periphery for a length coextensive with the U-shaped periphery of the body. The body has an integral center portion which arches upwardly from the U-shaped channel to conform to the similarly upwardly arched or convex form of the roof of the mouth or palate of the mouthpiece user. The U-shaped channel may be enclosed and filled with encapsulated setting materials to form a permanent, form-fitting dental impression for the upper teeth of a user. A medicated pad may be adhesively positioned over the enclosed channel to relieve sore gums and teeth. The storage container is constructed of rigid polymeric material and has a U-shape complementary to that of the mouthpiece for receiving the mouthpiece and a sufficient amount of a fluid solution of sterilizing, mouth-refreshing, and medicating ingredients to soak the mouthpiece therein between uses.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the included abstract is to enable the U.S. Patent and Trademark Office and the public generally, and especially the scientists, engineers, and practitioners in the art who are not familiar with patent or legal terms or phraseology, to determine quickly from a cursory inspection, the nature and essence of the technical disclosure of the application. The abstract is neither intended to define the invention of the application, which is measured by the claims, nor is it intended to be limiting as to the scope of the invention in any way.

It is therefore an object of the invention to provide a new and improved apparatus for protecting and treating teeth which has all the advantages of the prior art oral protective and treatment devices and none of the disadvantages.

It is another object of the present invention to provide a new and improved apparatus for protecting and treating teeth which may be easily and efficiently manufactured and marketed.

It is a further object of the present invention to provide a new and improved apparatus for protecting and treating teeth which is of durable and reliable construction.

An even further object of the present invention is to provide a new and improved apparatus for protecting and treating teeth which is susceptible of a low cost of manufacture with regard to both materials and labor, and which accordingly is then susceptible of low prices of sale to the consuming public, thereby making such apparatuses for protecting and treating teeth economically available to the buying public.

Still yet another object of the present invention is to provide a new and improved apparatus for protecting and treating teeth which provides in the apparatuses and methods of the prior art some of the advantages thereof, while simultaneously overcoming some of the disadvantages normally associated therewith.

Still another object of the present invention is to provide a new and improved apparatus for protecting and treating teeth having a mouthpiece which effectively prevents the unconscious gnashing or gritting of teeth of a user during sleep.

Yet another object of the present invention is to provide a new and improved apparatus for protecting and treating teeth which effectively sterilizes, medicates, and deodorizes the teeth and gums of a user during sleep to prevent decay-causing build-up on the teeth and unpleasant mouth and breath odors.

Even still another object of the present invention is to provide a new and improved apparatus for protecting and treating teeth having a mouthpiece which is comfortable to wear and is form fitting to the teeth of each user to enable full contact therewith to maximize the intended functions of sterilizing, medicating, and deodorizing.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
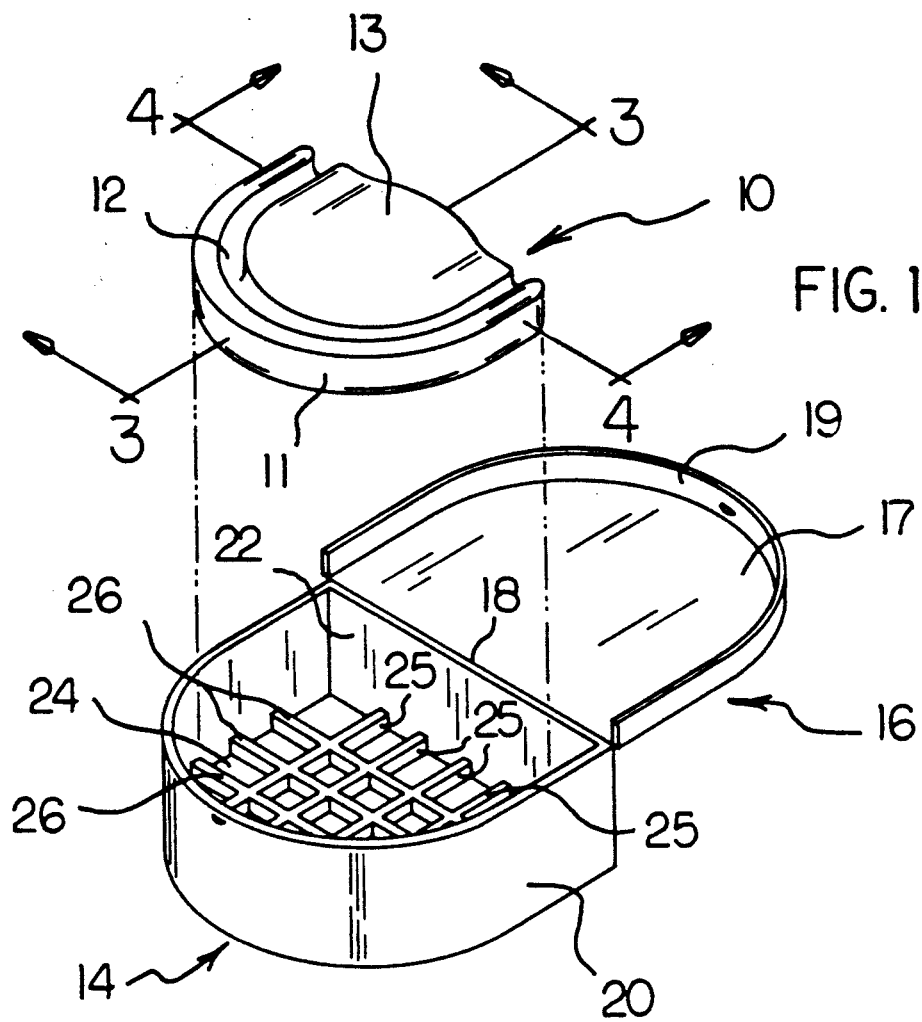
FIG. 1 is a perspective view of the mouthpiece and storage container of the present invention.

With reference now to the drawings, and in particular to FIGS. 1-8 thereof, a new and improved apparatus for protecting and treating teeth embodying the principles and concepts of the present invention and generally designated by the reference numerals 10,14,30 and 30' will be described.

Figure 2:
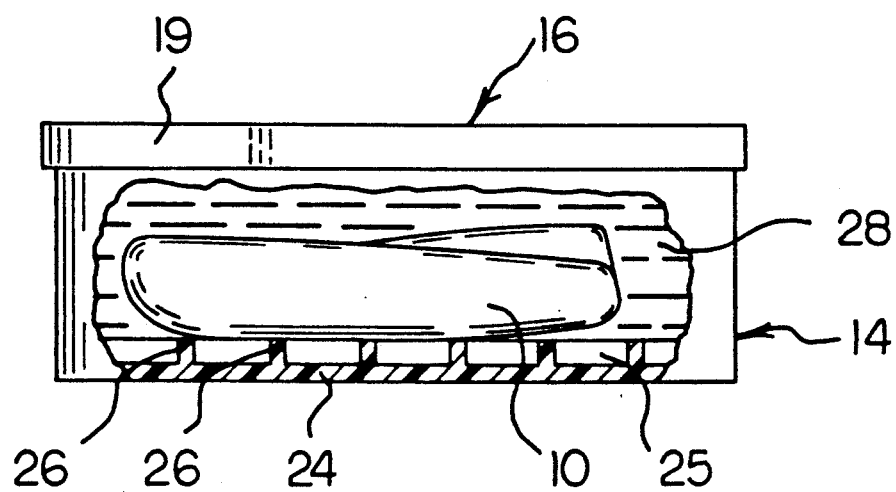
FIG. 2 is a side elevational view of the storage container of the present invention in the closed condition with a portion of its arcuate side wall broken away to show the mouthpiece immersed in the sterilizing, cleansing, and deodorizing or mouth-refreshing solution.
Figure 3:
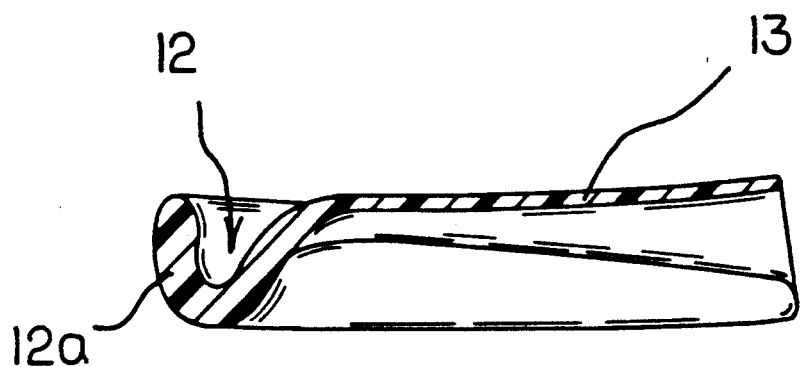
FIG. 3 is a cross-sectional view of the mouthpiece of the present invention taken along line 3—3 in FIG. 1.
Figure 4:
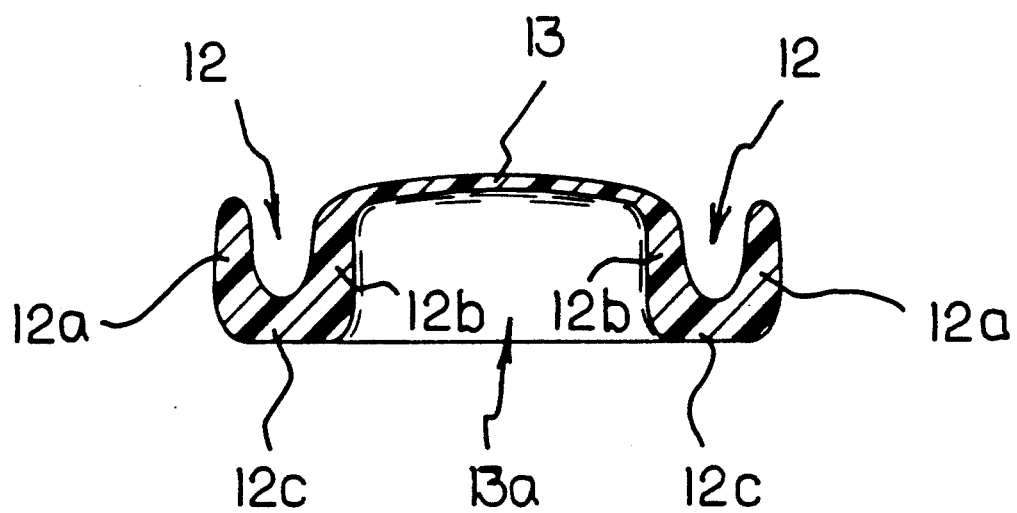
FIG. 4 is a cross-sectional view of the mouthpiece of the present invention taken along line 4—4 in FIG. 1.

More specifically, and with particular reference to FIGS. 1 and 2, mouthpiece 10 of the inventive apparatus is provided with an arcuate or U-shaped body 11 having a continuous U-shaped channel 12 formed therein. Body 11 is preferably molded from a relatively thin layer of soft, pliable, and absorbent elastomeric material to provide a lightweight and comfortable fit in the mouth of the user. Channel 12 is positioned adjacent the periphery of body 11 and has a length coextensive with the U-shaped periphery of body 11. As illustrated in FIGS. 1, 3, and 4, channel 12 is defined by a pair of substantially parallel, upstanding legs 12a,12b joined at their lower ends by a connecting leg 12c. Channel 12 is dimensioned for receiving the upper teeth of the user. Body 11 has an integral center portion 13 wherein its outer surface arches upwardly or convexly from channel 12 and its inner surface arches downwardly to form a concavity 13a. This arched central portion 13 conforms to the complementary arched shape of the roof of the mouth or palate of the mouthpiece 10 user thereby providing a comfortable fit therein.

Between sleeping uses, mouthpiece 10 is stored in a container 14 which is also U-shaped in a complementary manner to mouthpiece 10. Container 14 includes a U-shaped cover 16 having a planar top 17 with a longitudinal outer edge 18. A U-shaped flange 19 extends downwardly from the underside of planar top 17 at its U-shaped peripheral edge. Container 14 further includes a U-shaped base member comprising a U-shaped and upstanding wall 20, a flat rear wall 22 connecting the opposed ends of wall 20, and a bottom wall 24 connecting the adjacent bottom longitudinal edges of each wall 20 and 22. Integrally formed on and extending upwardly from bottom wall 24 within the base member are a first set of parallel and narrow ribs 25 and a second set of parallel and narrow ribs 26. Ribs 25 and 26 intersect each other at right angles to form an upstanding grid pattern on bottom wall 24. Cover 16 is pivotally connected to the base member at the integrally joined upper longitudinal edge of rear wall 22 at the open end of the base member and the outer longitudinal edge 18 of planar top 17. In the closed position (FIG. 2), planar top 17 completely encloses the base member and flange 19 overlies and contacts an upper portion of upstanding wall 20 along its entire periphery. Container 14 is preferably molded from a rigid polymeric material.

In use, cover 16 is opened to the position shown in FIG. 1. The base member is supplied with a cleansing fluid mixture 28 of sterilizing (bactericides) and mouth-refreshing ingredients such as flavorings of the type used in conventional mouth washes. Mouthpiece 10 is placed in the base member and cover 16 is closed. The amount of cleansing fluid 28 placed in the base member must be sufficient to completely submerge mouthpiece 10 therein in the manner shown in FIG. 2. The provision of ribs 26 on bottom wall 24 allows maximum contact between mouthpiece 10 and fluid 28 to provide improved cleansing between uses as well as maximum absorption of fluid 28 by the mouthpiece 10 during non-use or storage periods. Furthermore, ribs 26 provide extra rigidity for the bottom wall 24, and also prevent sloshing of fluid 28 in container 14.

When mouthpiece 10 is ready for use, it is withdrawn from container 14 and positioned in the user's mouth in a manner wherein upper teeth are placed in U-shaped channel 12. Due to its lightweight, soft texture, and form-fitting configuration, its use during sleep is extremely comfortable and hardly noticeable. Furthermore, it effectively prevents unconscious contact or gnashing between the upper and lower teeth. Simultaneously, since mouthpiece 10 has been thoroughly cleansed and saturated with fluid 28 during storage, the teeth are continuously contacted by fluid 28 during the entire use or sleeping period to effectively prevent the build-up of decay-causing film on the teeth, as well as the associated unpleasant mouth odors and tastes. Accordingly, when the user arises, mouthpiece 10 is removed from the upper teeth and replaced in container 14 for recleaning and sterilizing. After rinsing, the user's mouth is clean, fresh-tasting, and free of morning breath odors due to the treatment during sleep by clean and saturated mouthpiece 10.

Figure 5:
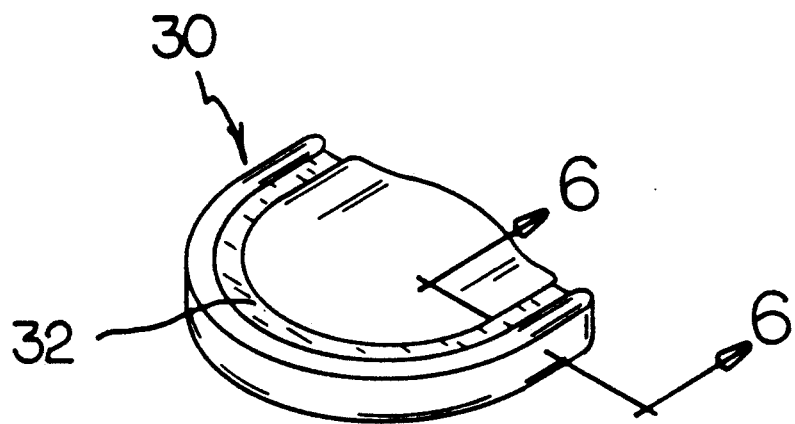
FIG. 5 is a perspective view of a second embodiment of the mouthpiece of the present invention.
Figure 6:
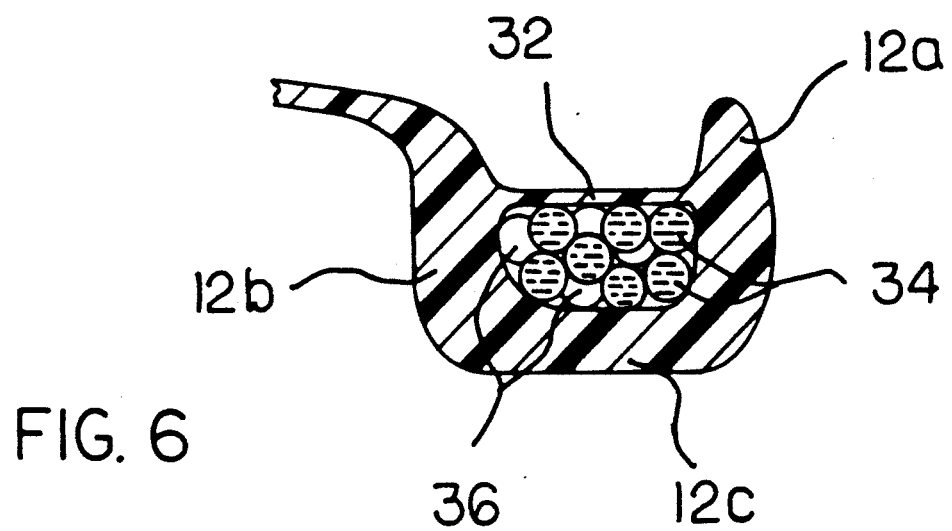
FIG. 6 is a cross-sectional view of the second embodiment of the mouthpiece of the present invention taken along line 6—6 in FIG. 5.

Referring now to FIGS. 5 and 6, a second embodiment of the mouthpiece of the inventive apparatus is shown. Mouthpiece 30 is substantially similar in general structural arrangement to mouthpiece 10 of the first embodiment. The structural difference of mouthpiece 30 is the provision of a web 32 which covers and encloses a major portion of U-shaped channel 12. Web 32 extends integrally between legs 12a and 12b at a position below their upper ends in overlying relationship with connecting leg 12c to form a covered or tubular U-shaped channel (FIG. 6). Packed within the tubular, U-shaped channel are the ingredients required to form a permanent impression of the upper teeth, i.e. an exact contour of the upper teeth of the user. Those ingredients include a first plurality of gelatin capsules 34 containing, for example, an acrylic liquid, and a second plurality of gelatin capsules 36 containing, for example, an acrylic powder. When mixed together, these ingredients provide a self-setting filler for forming a permanent dental impression or exact form-fitting contour of the upper teeth of the user therein. Fillers of this type are well known in the art. In use, the user removes saturated mouthpiece 30 from fluid 28 in container 14 and positions upper teeth in channel 12. The user's jaws are closed and upper teeth are guided into channel 12 by the upper ends of legs 12a,12b and are pressed downwardly against web 32 and capsules 34,36 to break the capsules, mix the filler ingredients, and press the upper teeth into the filler and form the dental impression therein. The jaws are held in the closed position until the impression is permanently set by the user's body heat. Since the filler chemically bonds to the surrounding surfaces of channel 12, web 32 thereof also conforms permanently to the formed impression. In this manner, channel 12 is provided with a configuration which conforms exactly to the shape of each user's mouth thereby maximizing comfort as well as surface contact of the treating fluid 28 with mouthpiece 30 during storage and the adjacent surfaces of the teeth and mouth during use.

Figure 7:
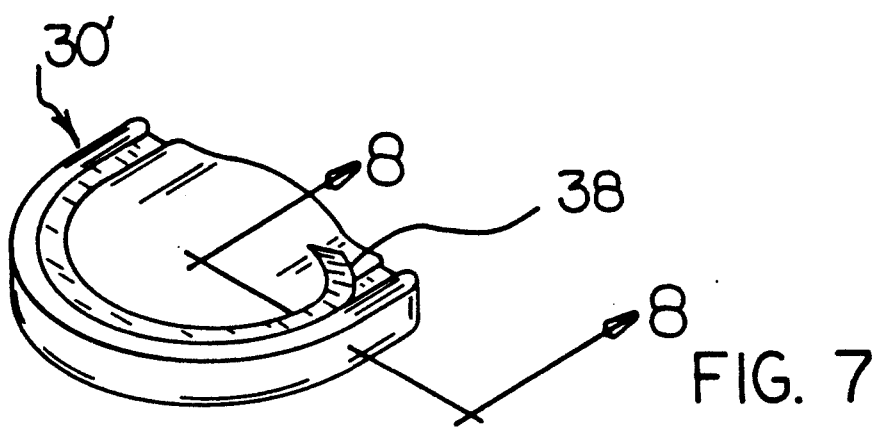
FIG. 7 is a perspective view of a third embodiment of the mouthpiece of the present invention.
Figure 8:
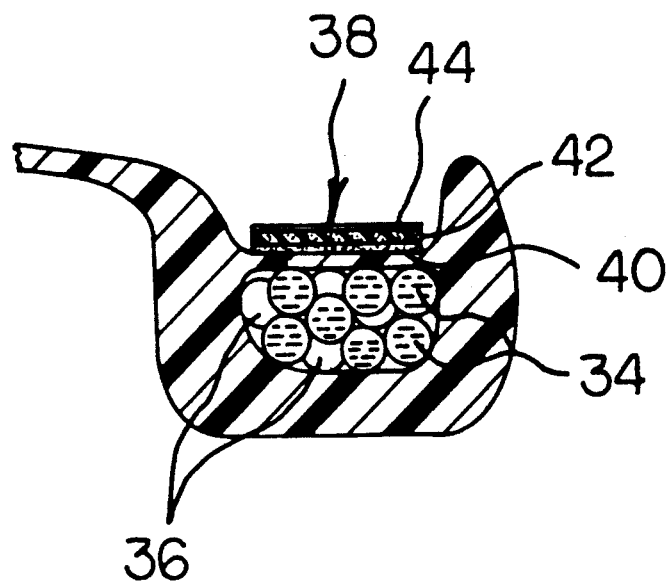
FIG. 8 is a cross-sectional view of the third embodiment of the mouthpiece of the present invention taken along line 8—8 in FIG. 7.

FIGS. 7 and 8 illustrate a third embodiment of the mouthpiece of the inventive apparatus. Mouthpiece 30' is substantially structurally identical to mouthpiece 30. The oral condition of soreness of the teeth and gums is quite common. Accordingly, in order to increase the functional use of mouthpiece 30 by relieving this condition, a U-shaped medicated pad 38 having three distinct layers and the same shape as channel 12 is adhesively applied to web 32, either before or after the formation of the impression previously described to provide a mouthpiece 30'. Pad 38 includes a first layer comprising a thin layer of adhesive 40, a second and intermediate layer 42 of absorbent polymeric or fabric material saturated with a medicating substance, and a third smooth, non-porous outer layer 44, preferably of polymeric material, to facilitate pressing of pad 38 on web 32. In use, when mouthpiece 30' is placed in the user's mouth and the jaws are closed, medicating substance is released from layer 42 to treat the teeth and gums. A plurality of pads 38 may be provided so that one may be easily stripped from web 32 after each use, and a new one applied before the next use. Alternatively, mouthpieces 10 and 30 may be prepared for medicating the teeth and gums by adding a medicating ingredient to fluid 28 in storage container 14.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function, and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An apparatus for protecting and treating teeth comprising, in combination:
   a mouthpiece including:
   a substantially U-shaped body having an outer periphery;
   a substantially U-shaped channel formed in said body in a position adjacent to and spaced inwardly from said outer periphery, wherein said U-shaped channel is coextensive with said outer periphery and dimensioned to receive upper teeth of a user;
   a web extending integrally between said opposed legs for enclosing said legs and thereby forming a tubular U-shaped channel;
   setting materials positioned within and filling said tubular U-shaped channel for forming a permanent dental impression of said upper teeth therein;
   a medicated U-shaped pad adhesively positioned on said web; and
   an integral central portion having an outer surface and an inner surface, wherein said outer surface arches upwardly in a convex manner with respect to said U-shaped channel to define an outer surface contour complementary in shape to a palate of said user, and wherein said inner surface defines a concavity between opposed legs of said U-shaped channel; and
   a storage container for receiving and treating said mouthpiece during periods of non-use, said storage container comprising:
   a U-shaped base member which is complementary in shape and dimensioned to receive said mouthpiece therein;
   a U-shaped upstanding wall having a pair of opposed ends;
   a flat rear wall extending between and joining said opposed ends of said U-shaped upstanding wall; and
   a bottom wall extending between and connected to bottom longitudinal edges of said U-shaped upstanding wall and said flat rear wall.

2. The apparatus for protecting and treating teeth as set forth in claim 1,
   wherein said mouthpiece is formed of a soft, pliable, and absorbent elastomeric material.

3. The apparatus for protecting and treating teeth as set forth in claim 1,
   wherein said setting materials comprise a first plurality of capsules containing an elastomeric powder, and a second plurality of capsules containing a viscous elastomeric liquid.

4. The apparatus for protecting and treating teeth as set forth in claim 1,
   wherein said medicated U-shaped pad is coextensive with said U-shaped channel and comprises a first adhesive layer contacting said web, a second layer of absorbent material adjacent said first layer, said second layer being saturated with a medicating substance, and a third layer overlying and joined to said second layer, said third layer being formed of a relatively non-porous, polymeric material to enable pressing of said U-shaped pad on said web.

5. The apparatus for protecting and treating teeth as set forth in claim 1,
   wherein said storage container further includes support means integrally formed on and extending upwardly from said bottom wall in a position within said base member for maintaining said mouthpiece therein in spaced relationship from said bottom wall.

6. The apparatus for protecting and treating teeth as set forth in claim 5,
   wherein said support means comprises a plurality of spaced and narrow ribs which intersect each other to form an upstanding grid pattern on said bottom wall; and
   further including a quantity of sterilizing and cleansing fluid in said base member sufficient to cover and completely surround said U-shaped mouthpiece positioned in said base member and supported on said ribs.

7. The apparatus for protecting and treating teeth as set forth in claim 6,
   wherein said sterilizing and cleansing fluid further includes a medicating ingredient.

8. The apparatus for protecting and treating teeth as set forth in claim 1,
   wherein said storage container further includes a U-shaped cover complementary in form to said U-shaped base member, said U-shaped cover being hinged to an upper longitudinal edge of said flat rear wall; and
   wherein said storage container is formed of a rigid polymeric material.

9. The apparatus for protecting and treating teeth as set forth in claim 6,
   wherein said plurality of spaced ribs include a first set having a plurality of first parallel ribs, and a second set having a plurality of second parallel ribs, wherein said first parallel ribs of said first set and said second parallel ribs of said second set intersect each other at right angles.

* * * * *